United States Patent [19]

Cook

[11] Plant 5,232

[45] May 15, 1984

[54] DISTINCT VARIETY OF STRAWBERRY PLANT—RUBY RED

[75] Inventor: Albert B. Cook, Rockport, Ind.

[73] Assignee: Herschel L. Boll, Champaign, Ill.

[21] Appl. No.: 406,378

[22] Filed: Aug. 9, 1982

[51] Int. Cl.[3] ..... A01H 5/03

[52] U.S. Cl. ..... Plt./48

[58] Field of Search ..... Plt./48

*Primary Examiner*—Robert E. Bagwill

*Attorney, Agent, or Firm*—Marmaduke A. Hobbs

[57] ABSTRACT

A strawberry variety characterized by large plants bearing late-ripening, large fruit.

3 Drawing Figures

My invention relates to a new and distinct variety of strawberry plant. It is the result of a cross of [([(Canall × Twentieth Century) × Twentieth Century] × Ogallala) × Oberschlesien] × Surecrop, made by me in 1969, at Grandview, Ind.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. My new variety, which has the cultivar name of "Ruby Red", has proved itself to have unusual possibilities because of its very large plant, its late season of maturity, and its very large fruit.

Figure 1:
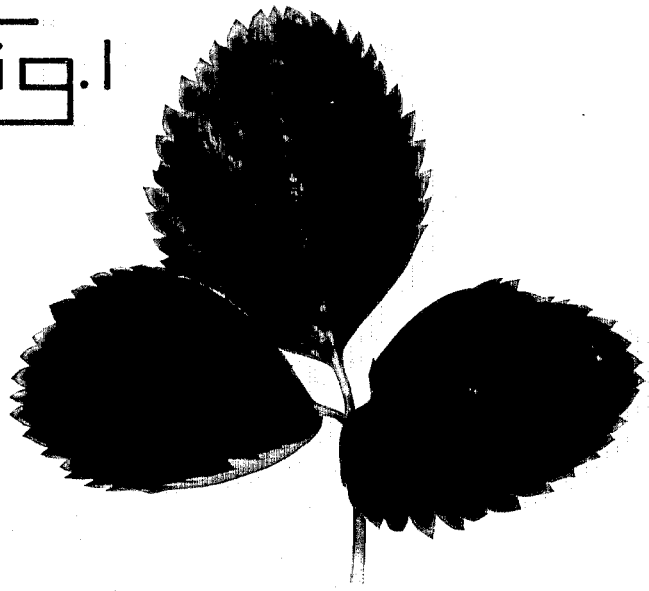
FIG. 1 shows a typical leaf in full color.
Figure 2:
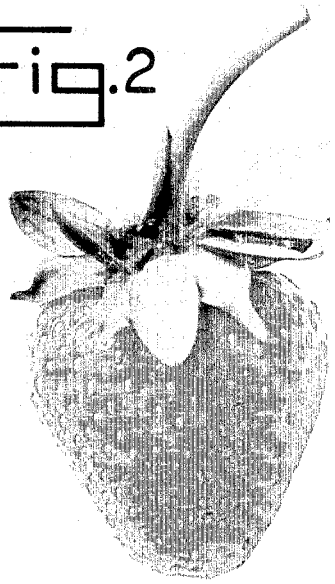
FIG. 2 shows a berry of typical shape.
Figure 3:
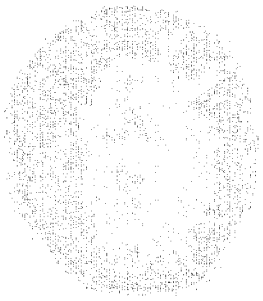
FIG. 3 illustrates a typical central cross-section of a berry.

In general, the distinct and new variety of strawberry plant, which is the subject of my invention and discovery, is charcterized by its very large plant, its late season of maturity, and its very large fruit. These characteristics I now refer to in greater detail. Color plate references are according to Color Standards and Color Nomenclature by Robert Ridgway.

Under conditions at Grandview, Ind., and at Champaign, Ill., my new variety of plant is June-bearing and medium in productivity. The plants are very large (larger than Surecrop and Jerseybelle), and are very tall, measuring up to 15 inches in height and averaging about 11 to 12 inches. In general, they produce a medium number of runners (about 15 to 20 per plant — less than Surecrop); however, during an occasional season, they have produced only about 5 per plant.

The leaves are medium green in color, or are approximately Forest Green (Plate XVII), or varying from Varley's Green (Plate XVIII) to Forest Green (Plate XVII) to Cerro Green (Plate V), depending mainly on soil fertility, but also depending on other soil conditions, exposure, and weather and climatic conditions. The leaves are very large (up to 8½ inches in width and averaging about 6 to 7 inches), slightly glossy, very cupped, and relatively smooth. The terminal leaflet overlaps the lateral leaflets, and the lateral leaflets overlap at the base of the leaf. The petioles are thick, up to 3/16 inch in diameter. The flowers are perfect and are very large, up to 2 inches in diameter. The date of the first blossoms in 1981 in southwestern Michigan was May 13.

At Grandview, Ind., and at Champaign, Ill., my new variety of strawberry plant begins to mature its fruit late, about 9 to 10 days later than Surecrop and about 3 to 4 days later than Jerseybelle. The date of the first picking in 1981 in southwestern Michigan was June 12. The harvesting period is medium in length, or about 14 to 21 days. The berries are well formed throughout the bearing season.

The fruit is medium red (Jerseybelle is much darker), or is approximately Nopal Red (Plate I), or varying from Jasper Red (Plate XIII) to Nopal Red (Plate I) to Carmine Red (Plate I), depending mainly on exposure, but also depending on soil, weather, and climatic conditions. The fruit is very large (up to 2 inches in diameter and averaging about 1¼ to 1½ inches), and the size is maintained well during the picking season. The primary berries are wedge to conic in shape, while secondary and later berries are mostly conic. About half of the fruit is slightly necked. Occasionally, a large berry is slightly necked with an enlargement of the flesh at the base of up to 20% of the stamens. The fruit is glossy and very firm. The fruit stems are thick (up to 3/16 inch in diameter) and long (up to 11 inches).

The calyx is large. An occasional sepal is 3-toothed instead of single-toothed. The achenes are about flush with the surface to slightly raised, and are yellow to red depending on exposure.

Under the conditions existing where I have reproduced and tested my new variety of strawberry plant, the flesh of the berry is medium light red to medium red. The flesh of Jerseybelle is much darker. Usually there is a short pinkish core surrounded by a hollow area, which is surrounded by a slight pinkish area. The fruit is relatively sweet, and is slightly above average in flavor.

My new variety of strawberry plant is not especially resistant to any of the diseases. The strawberry above described, and the plant producing it, of course, may vary in slight details, depending on soil, weather, and climatic condition.

What I claim is:

1. A new and distinct variety of strawberry plant substantially as herein shown and described, characterized by its very large plant, its late season of maturity, and its very large fruit.

* * * * *